United States Patent
Osypka

(10) Patent No.: US 6,964,677 B2
(45) Date of Patent: Nov. 15, 2005

(54) IMPLANTABLE STENT

(76) Inventor: Peter Osypka, Basler Strasse 109, Grenzach-Wyhlen (DE), D-79630

( * ) Notice: Subject to any disclaimer, the term of this patent is extended or adjusted under 35 U.S.C. 154(b) by 419 days.

(21) Appl. No.: 10/062,114

(22) Filed: Jan. 31, 2002

(65) Prior Publication Data
US 2002/0128706 A1 Sep. 12, 2002

(30) Foreign Application Priority Data
Feb. 6, 2001 (DE) .......................... 101 05 160

(51) Int. Cl.[7] ................................. A61F 2/06
(52) U.S. Cl. ....................... 623/1.11; 606/108
(58) Field of Search ................. 606/153, 154, 606/194, 198; 623/1.15, 1.16, 1.17, 1.18, 1.19, 1.2, 1.36, 1.11, 1.3

(56) References Cited

U.S. PATENT DOCUMENTS

| 4,776,337 A | | 10/1988 | Palmaz | |
| 5,041,126 A | * | 8/1991 | Gianturco | 623/1.15 |
| 5,133,732 A | * | 7/1992 | Wiktor | 623/1.22 |
| 5,554,181 A | * | 9/1996 | Das | 623/1.12 |
| 5,591,223 A | * | 1/1997 | Lock et al. | 623/1.17 |

FOREIGN PATENT DOCUMENTS

| DE | 101 03 000 | 8/2002 |
| EP | 0246998 A2 | 11/1987 |
| JP | 08103501 A | 4/1996 |
| WO | WO0045738 | 8/2000 |

* cited by examiner

Primary Examiner—Julian W. Woo
Assistant Examiner—Victor Nguyen
(74) Attorney, Agent, or Firm—Volpe and Koenig, P.C.

(57) ABSTRACT

An implantable stent (10) which is installed as a support sleeve in the region of an vasoconstriction expandable especially by means of a balloon catheter (2), is continuously broken along the one long side. On both sides of the break (4), recesses, eyelets or punchings (6) are provided on which at least one removable holding element engages in order to keep the break (4) closed at first. After removing the holding element by withdrawing or gradual dissolution of its material, the break (4) can be exposed so that the previously selected stent (1) can be subsequently expanded again while enlarging the break (4) in order, for example to take the growth of a patient into consideration.

11 Claims, 6 Drawing Sheets

IMPLANTABLE STENT

BACKGROUND

The invention concerns an implantable stent which is insertable as a support sleeve in the region of a vascular constriction, especially of the type expanded by a balloon catheter, whereby the stent is expandable radially and is open or broken continuously along at least one longitudinal side or meridian line.

Such a stent is known from EP 0 246 998 A2. Here in the initial position the edges on the open longitudinal side overlap and the stent can only be expanded in that this overlapping is diminished. This takes place against the elastic restoring forces of the material of the stent, and on the one longitudinal edge, grooves are provided into which the other longitudinal edge can be pressed in at all times under the material tension and the pressure of the vessel wall. This means on the one hand a relatively expensive manufacture and on the other hand only a relatively minor expandability. Furthermore, the expansion must take place very precisely so that the one longitudinal edge can in any given case engage in the internal longitudinal grooves of the other longitudinal edge. Finally, only step-wise expansions are possible, whereby the steps correspond to the spacings of the internal longitudinal grooves.

In addition, stents made with perforations about their periphery which is made of metal are known. These have a web or meandering structure such that a radial expansion is possible through appropriate deformations. Such stents which resemble a wire cage which can be expanded in the vessels themselves are implanted, for example, in infants with congenital heart defects or, also in many cases with adults. A previously unsolved problem consists in that a subsequent, if need be repeated reexpansion, that is, an enlargement of the periphery of the stent or support sleeve, for example, conditioned by growth in children, is not possible after a certain expansion stage. The consequence of this is that, due to the stent, an artificial constriction of the vessel can subsequently take place.

SUMMARY

Underlying the invention is therefore the object of creating a stent of the type mentioned at the beginning which, after implantation and expansion, later allows one or more further dilitations, for example for adaptation to the growth of a patient or for renewed expansion or a recurring stenosis, whereby a largely continuous dilitation should be possible.

The solution of this apparently contradictory objective is the implantable stent described at the beginning with at least one break or opening in the longitudinal side, wherein the wall of the stent is expandable, wherein in the edges provided on both sides of the break, running axially, in any given case recesses, eyelets or punchings are provided, and wherein in a first working position, the recesses, eyelets or punchings are covered or penetrated by at least one removable holding element and in this way, the break is held at the specified slot spacing or closed.

With a stent or support sleeve of this type, it is possible to fix in position a widened vascular constriction since the stent itself is dilated in the usual manner, and since its walling is expanded. The holding element can here still be in a working position. Accordingly, it can then be removed in a suitable manner, in that, for example, it is pulled out or it dissolves by itself in the course of time. Later this makes a further dilitation possible without having to replace the stent since it can then be expanded by enlarging the break or opening.

Here it is especially beneficial if the break extends axially in the stent and has a wave-like or zig-zag or meander-like course and engages with tongues of the one edge formed in this manner projecting peripherally in any given case between the tongues of the other edge with an opposite peripheral orientation, and if the recesses, punchings or eyelets are at all times arranged in these tongues. This leads to a break of the stent which indeed basically extends axially on a sleeve line or sleeve surface, whereby, however, a mutual overlapping arises in connection with an aligning surface so that a subsequent further dilitation which is equal to or smaller than the axial extension of these tongues, leads to a bracing of the vessel wall even in the region of the break, although an even greater redilation is also possible.

The punchings, recesses or eyelets of the two edges of the break interdigitated by means of tongues or the like with each other can basically all be arranged on an approximately axially running line and be acted upon by an axially and/or radially oriented holding element. Such a holding element, if need be guided approximately wavelike alternating from above and below through the eyelets and punches of the tongues lying alongside one another, can subsequently, for example, also already be withdrawn after a first dilation or be made of a material which dissolves of itself so that a subsequent redilation is possible in a simple manner.

The removable holding element serving to hold the break or separation position together can thus be a thread, a plastic band or, with overlapping of the punchings, a large number of rivets and can be formed of a material or plastic which dissolves in the body of a patient itself.

A modified possibility can be provided in that the removable holding element is a wire or stylet. A holding element of this type can be pulled out after the first implantation and expansion of the stent so that a subsequent further dilitation is possible without difficulty.

A thread serving as a holding element pulled through the eyelets arranged along the break that are generally axially aligned with one another, alternating from one edge to the other, can be a surgical sewing thread which especially runs back at least once from one front face of the stent to the other and from there once again through the eyelets or the like, whereby the beginning and end of the thread are connected with each other, especially tied with each other. Surgical sewing threads which gradually dissolve in the body of the patients are known, and it is especially simple and appropriate to undertake the preliminary connection of the break of the stent of the invention with such a surgical sewing thread which has great strength and makes possible a very simple application. Since is can be guided back and forth through the eyelets, this allows the implanted stent to be expanded for the first time by stretching its surface without the break being widened.

On the basis of the longitudinally penetrating break, the stent constructed as a support sleeve in working position can be constructed in a flat, unrolled form of its subsequent sleeve wall and surface, and can subsequently be bent or shaped into a support sleeve which can be held together on the facing edges following shaping of the support sleeve by means of recesses, openings, eyelets or the like, and a holding element connecting these, such as a wire, a thread or the like.

The break provided for a further dilitation (held together at first) thus also has a considerable advantage in connection with the manufacture of the stent because it can, to a certain extent, be manufactured as a two dimensional workpiece. Here it can, for example, be etched or manufactured in another manner as is also known from shearing foils in an electric razor apparatus. A quasi two dimensional or flat workpiece can basically be more simply manufactured and processed than a three dimensional workpiece, like the previously typical stent that is unbroken on the longitudinal edges with an expandable surface.

On at least one front face end of the stent, mobile, pliable or elastic connection elements can be provided for fixed of separable connection with an additional stent for continuing the stent in an approximately axial direction. Consequently, several stents can be arranged one behind the other for increasing flexibility. Here, the stents can also be selectively expanded in a row arrangement as needed, that is one stent can be dilated more or more often than the axially adjacent stent. Furthermore, vascular branchings can also be well treated in this manner.

An especially appropriate development of such a multiple arrangement of stents can be provided in that, on facing front faces of stents to be connected with one another, in any given case, eyelets or recesses or the like are provided which are connected through self-dissolving threads in particular. Through the selection of material of these threads or monofilaments, the time of dissolution can be determined in advance.

This particular row arrangement of stents can also be configured such that the axial length of the respective stent is relatively short and that it forms a ring rather than a sleeve, whereby then several rings arranged axially one behind the other and connected flexibly can form the entire stent, and the overall length can be predetermined or adapted to a particular need by more or less such "rings."

The stent of the invention can be made of metal, especially of steel or-self expanding- of shape memory alloy steel (nitinol). A stent made, for example, of steel or another metal can be expanded and later redilated in the previously mentioned manner with the aid of a balloon catheter. If it is made of a memory metal such as nitinol, this can be selected such that expands following implantation due to warming up and the first expansion takes place automatically, thus without expansion through a balloon. A subsequent redilation, for example with the aid of a balloon catheter, is possible, however, whereby then a further stent is to be inserted in this first stent in order to set the enlarged dimension.

Overall there results a stent which permits a subsequent, and/or several further dilations, for example for adaptation to the growth of a child, thus does not need to be removed in connection with a redilation and replaced by a new, larger stent.

BRIEF DESCRIPTION OF THE DRAWINGS

Embodiments of the invention are described in greater detail below on the basis of the drawings, wherein in part in schematic representation.

DETAILED DESCRIPTION OF THE PREFERRED EMBODIMENTS

Figure 7:
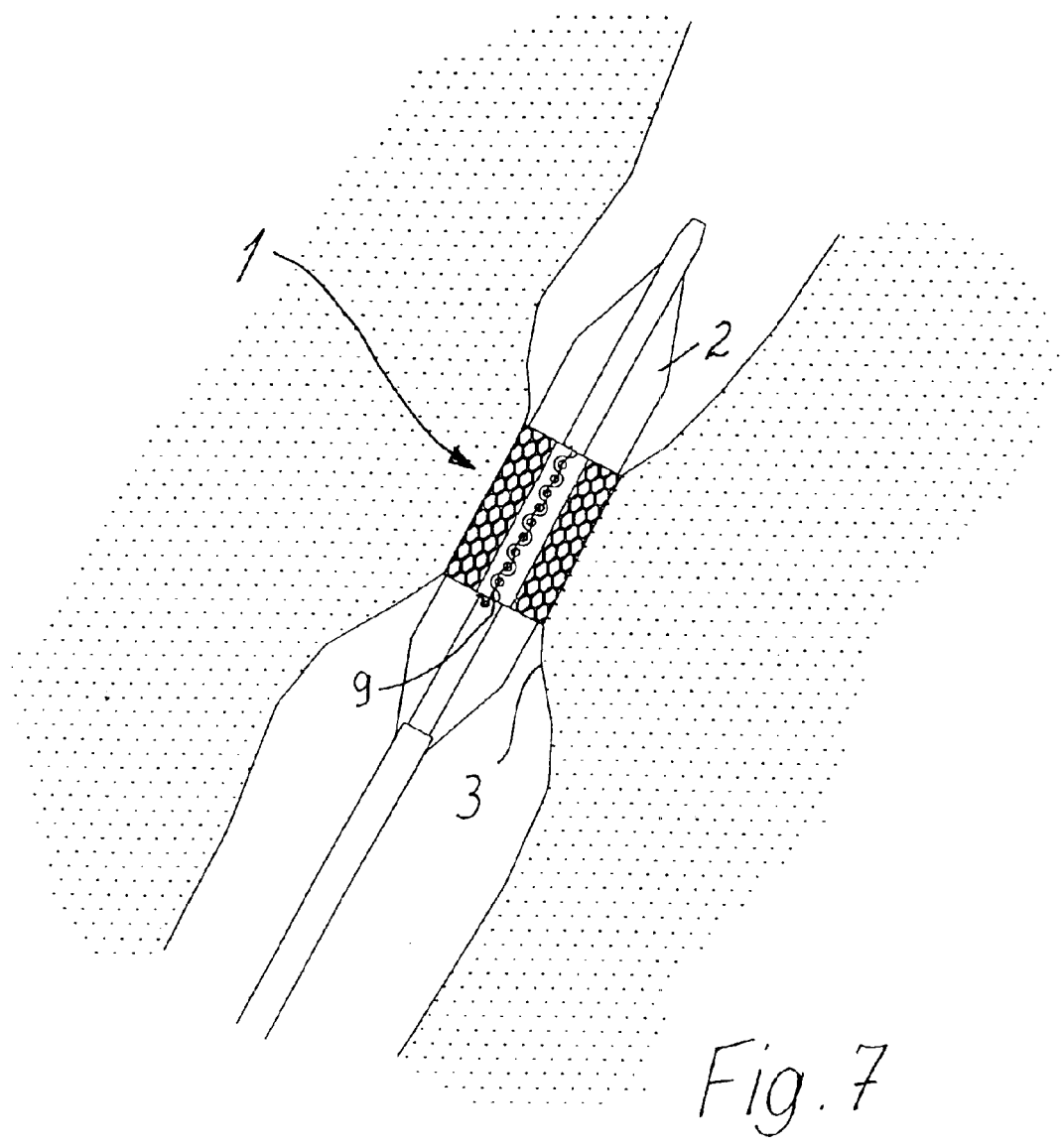
FIG. 7 is a view of the application and arrangement of a stent of the invention, in this case the embodiment according to FIG. 2, in the region of a vascular constriction during or at the end of a first dilation.
Figure 8:
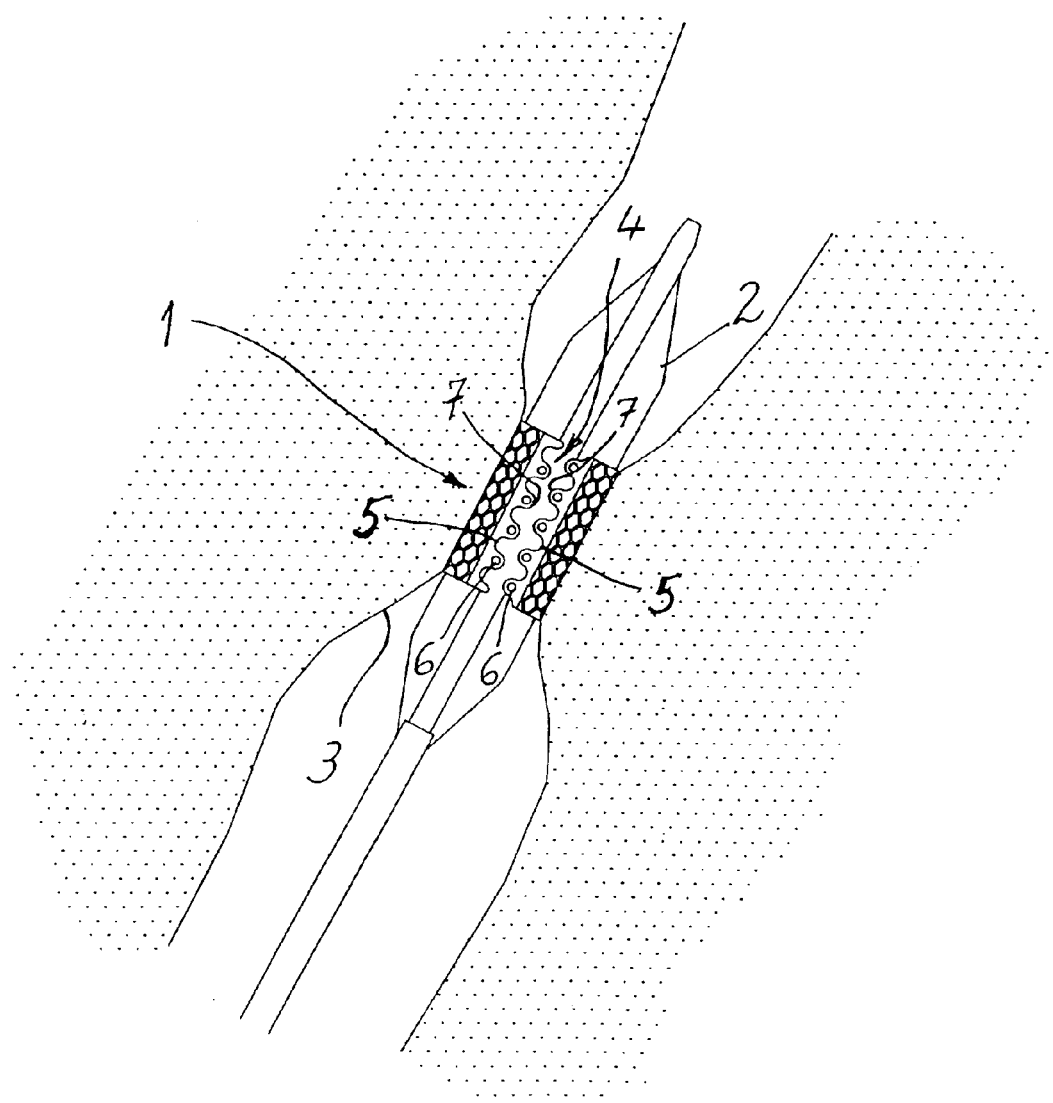
FIG. 8 is a view corresponding to FIG. 7, in which the stent, for example, is redilated after a long time, thus experiencing a repeated expansion in which the distance of the edges of the break is enlarged on the longitudinal side in accordance with this additional expansion.
Figure 9:
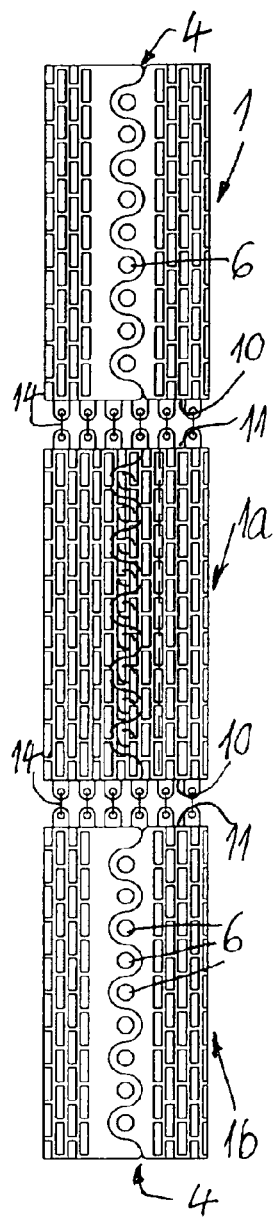
FIG. 9 is a side view of an embodiment in which several stents of the invention are connected with one another in a mobile but at first fixed manner.

A vascular support designated as a whole with 1, in the specialty occasionally also designated as a "stent," is insertable in accordance with FIGS. 7 and 8 as well as 12 as a support sleeve in the region of a vascular constriction 3 and expanded especially by means of a balloon catheter 2 so that this vascular constriction 3 retains its expanded position. For this, the stent 1 is radially expandable in relation to its initial position represented in FIG. 1 to 5, as is indicated in FIGS. 7 and 8 as well as in part in FIGS. 10 and 11. Here, these stents 1 are made of a sieve-like metal element in a familiar manner which enables a radial expansion through corresponding deformations of the bars forming the wall.

The stent 1 has a continuous opening or is broken open along a longitudinal side in all of the embodiments, which is especially recognizable in FIG. 8 in which a stent 1 of this type has been subsequently redilated following a first dilation in accordance with FIG. 7.

On the edges 5 extending axially on both sides of the break 4, one will recognize in any given case recesses, punchings or eyelets 6 which are constructed as circular holes or openings and are designated as "punchings 6" in the following.

These punchings 6 on both edges 5 are penetrated in an initial position or first working position in accordance with FIG. 1 to 7 as well as 9 to 12 by a removable holding element to be explained in greater detail below so that the break 4 is kept closed in the embodiments mentioned. Of course, it would also be conceivable for the break 4 fixed in this position by one or more holding elements to have a specified slot spacing of its edges 5 from the start.

Such a stent can be introduced in accordance with FIG. 7 into a vascular constriction and widened by means of a balloon catheter without the break 4 opening because the holding element remains effective. The dilation or expansion takes place through the structure of the walling of the bars forming the stent 1 which are arranged lattice-like or sieve-like in a known manner. Upon comparison of FIG. 7 with FIG. 2, one clearly recognizes how the structure of the walling of the stent 1 has changed due to this first dilation.

If a subsequent redilation is necessary due to the growth of a patient or for other reasons, the holding element can be removed, either in that this takes place already following the first dilation or in that it consists of a gradually dissolving material according to which the redilation recognizable in FIG. 8 can be conducted while enlarging the spacing of the edges 5, and consequently while enlarging the break 4. A removal of the stent 1 and replacing it by a larger stent or other difficult manipulations can thus simply be avoided.

In the embodiments represented, it is provided that the break 4 running axially or in the longitudinal direction has a wave-like and/or zig-zag or meander-like course, and tongues 7 of the one edge 5 formed in this way projecting in the peripheral direction engage in any given case between the tongues 7 extending in the opposite direction from the other edge 5. The break 4 thus has edges interdigitated with one another longitudinally. The punchings 6 are arranged in these tongues 7. It is above all especially clear in FIG. 1 that the punchings 6 of the two edges indented with each other by means of tongues 7 are all arranged on a line running approximately axially and can be acted upon by an approximately axially running line. Consequently such a holding element can also easily be retracted after implanting and the first expansion of these stents 1 in an axial direction in order to prepare for a subsequent redilation.

Figure 1:
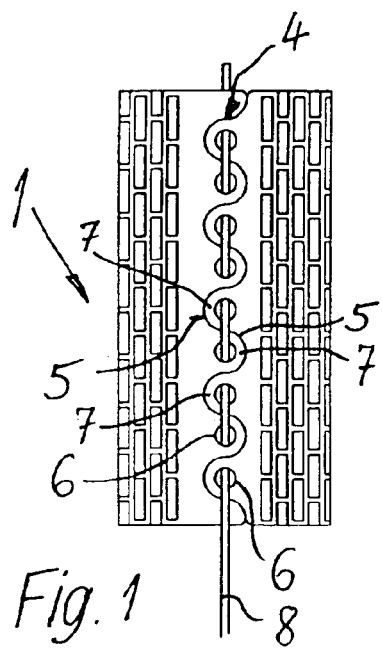
FIG. 1 is a side view of an implantable stent of the invention which has a break in the longitudinal direction which is kept closed by a removable holding element, whereby a wire or stylet serves as the holding element.

Such an arrangement is, for example, represented in FIG. 1 and provides that the removable holding element is a wire or stylet 8.

Figure 2:
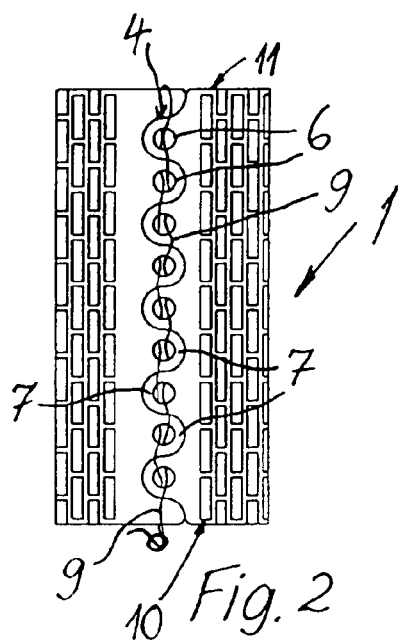
FIG. 2 is a side view of a stent corresponding to FIG. 1, whereby a surgical thread passed back and forth through alternating punchings or eyelets lying alongside one another serves as the holding element.

In contrast, FIGS. 2 and 7 show an embodiment in which the removable holding element serving to hold the break 4 or separation point together is a thread 9 of a material or plastic which dissolves in the body of a patient itself. For example, this thread 9 drawn through the punchings 6 arranged axially beside one another along the break 4, alternating to the one and to the other edge 5 can be a surgical sewing thread which runs from the one front face 10 of the stent 1 to the other front face 11-in any given case through the punchings 6 and there again back through the holes 6 so that a double thread ply arises. On the front face 10, beginning and end of the thread 9 are connected with each other, for example tied.

Figure 4:
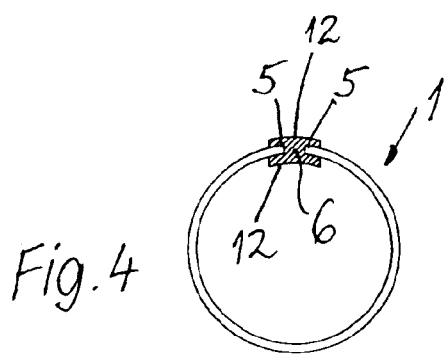
FIG. 4 is a cross section of the stent in accordance with FIG. 3.
Figure 3:
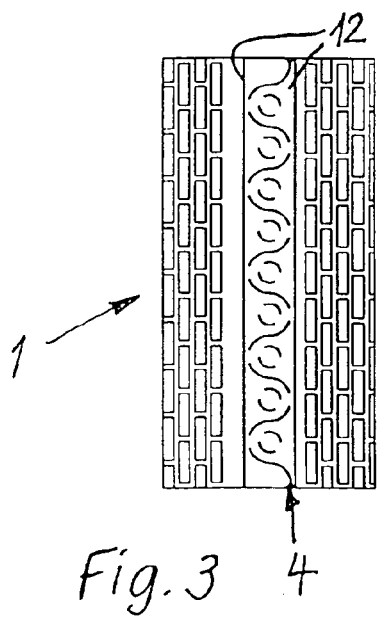
FIG. 3 is a view of a further modified embodiment with respect to the holding element in which a plastic band runs in the region of the break overlapping at least in the longitudinal direction on the interior as well as the exterior, and both plastic bands are connected with each other through eyelets or punchings arranged on the edges of the break, whereby it is formed of a plastic which dissolves in the course of time in the body of a patient.

FIGS. 3 and 4 shows an embodiment in which the removable holding element serving to keep the break 4 together is a plastic band 12 arranged on both sides whose plastic material passes through the punchings 6 so that practically two plastic bands 12, running on the one hand in the interior, and on the other hand on the exterior of the stent 1, are joined with each other and in this way hold the break together. This plastic can also dissolve in the course of time and in this way bring about the removal of the holding element.

Figure 6:
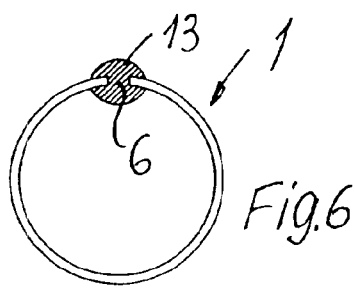
FIG. 6 is a cross section through the sleeve-like stent in accordance with FIG. 5.
Figure 5:
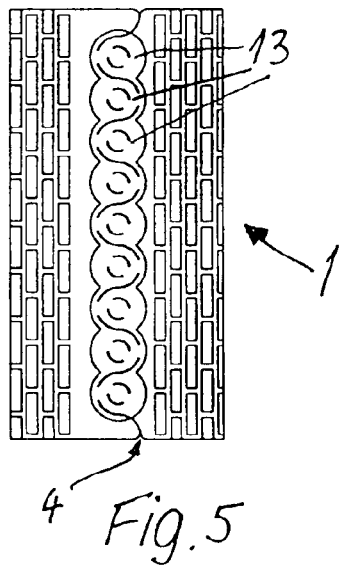
FIG. 5 is a side view of an embodiment corresponding approximately to FIG. 4, whereby in the region of the break and the punchings which overlap there, plastic rivets are installed of a plastic which dissolves in the body of the patient in the course of time.

FIGS. 5 and 6 show an embodiment in which the punchings 6 are connected by plastic rivets 13 of a self-dissolving plastic, the heads of which can be connected or fused with one another if need be in the longitudinal direction. Even in this case, the removal of the holding element takes place by the dissolution of the material.

It is easily discernable, chiefly on the basis of FIG. 8, that the stent 1 is constructed in a flat, unrolled form and can be shaped into a support sleeve which is held together on the edges 5 facing each other after forming the sleeve shape by means of recesses, openings, eyelets or punchings 6 and a holding element connecting these, such as wire, stylet 8, thread 9 or the like. The break thus considerably simplifies the manufacture of the support sleeve.

Figure 13:
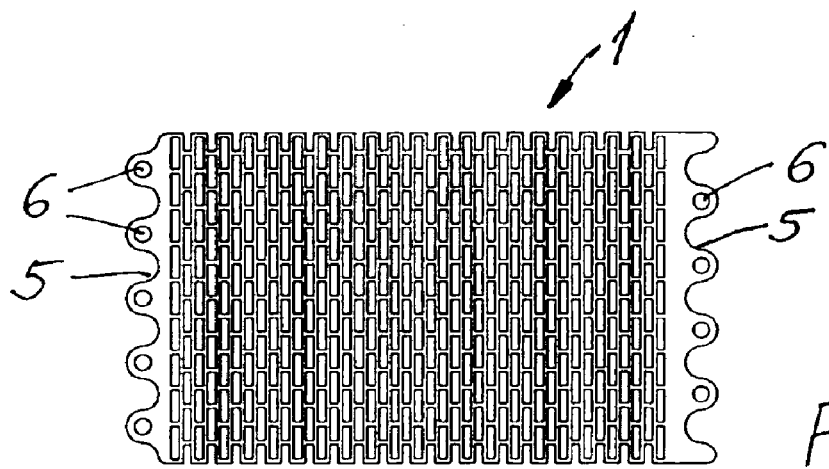
FIG. 13 is a view of a stent in accordance with FIGS. 1 to 8 as a flat pattern (unwound) prior to forming the sleeve shape.
Figure 14:
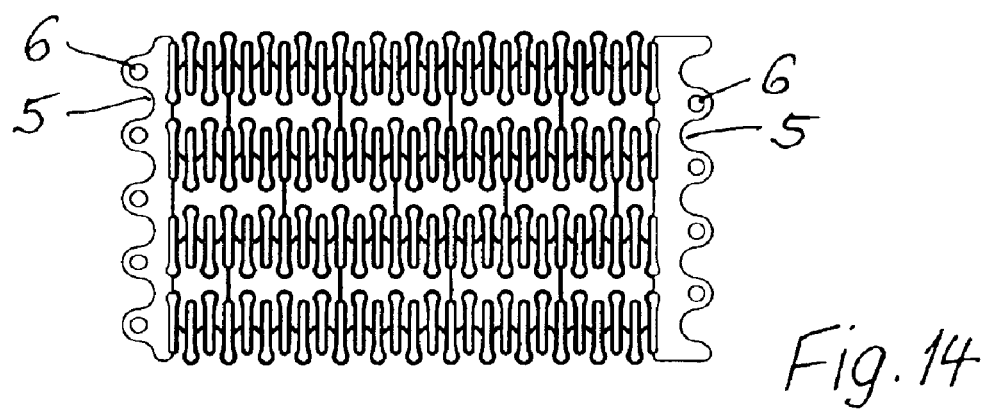
FIG. 14 is a view corresponding to FIG. 13 of a stent modified with respect to its wall structure.
Figure 15:
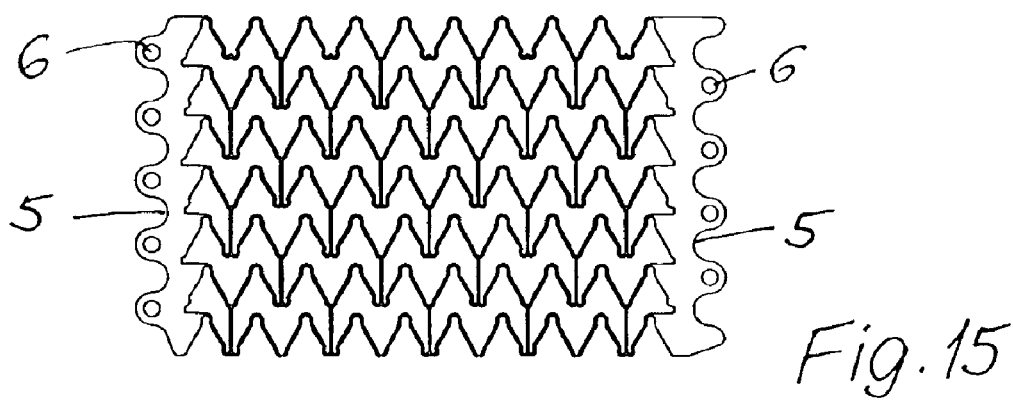
FIG. 15 is a view of a further configuration of a wall form of a stent still in an unwound state.

In FIGS. 13, 14 and 15, different examples of such an at first, flat unrolled form of a stent 1 of the invention prior to the formation of the sleeve shape and joining of break 4 then running longitudinally are represented. Here these embodiments differ only through the various bars forming the structure of the wall which make possible the radial expansion in an inherently familiar manner.

Figure 10:
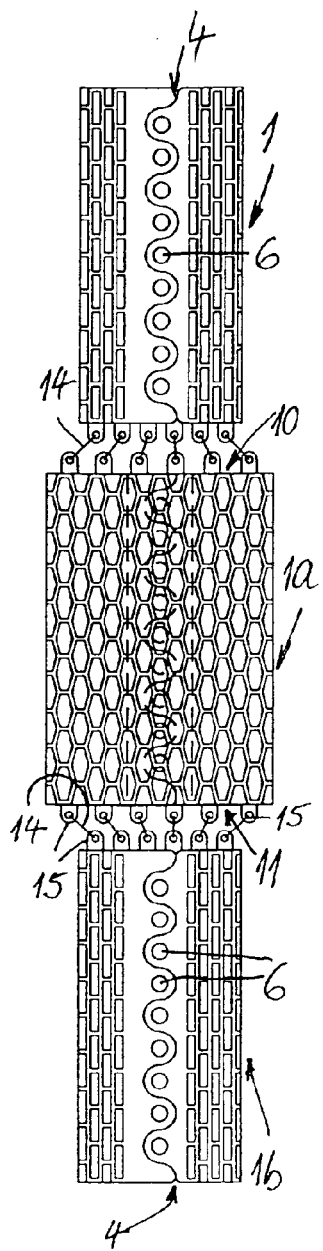
FIG. 10 is a side view of an embodiment corresponding to FIG. 9 in which the central of three continuous stents is dilated.
Figure 11:
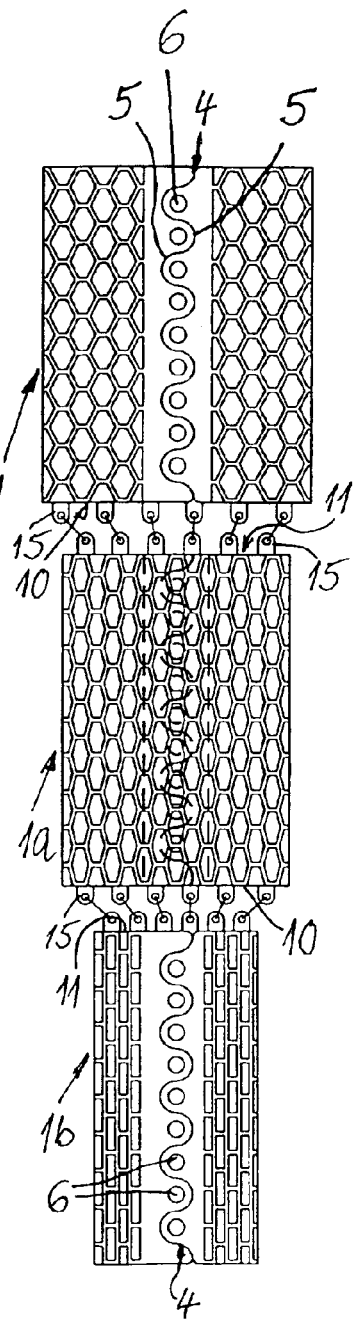
FIG. 11 is a side view of an arrangement in accordance with FIG. 9 in which the uppermost stent in this representation is most strongly dilated, the adjacent one somewhat less so, and the third is not dilated at all.
Figure 12:
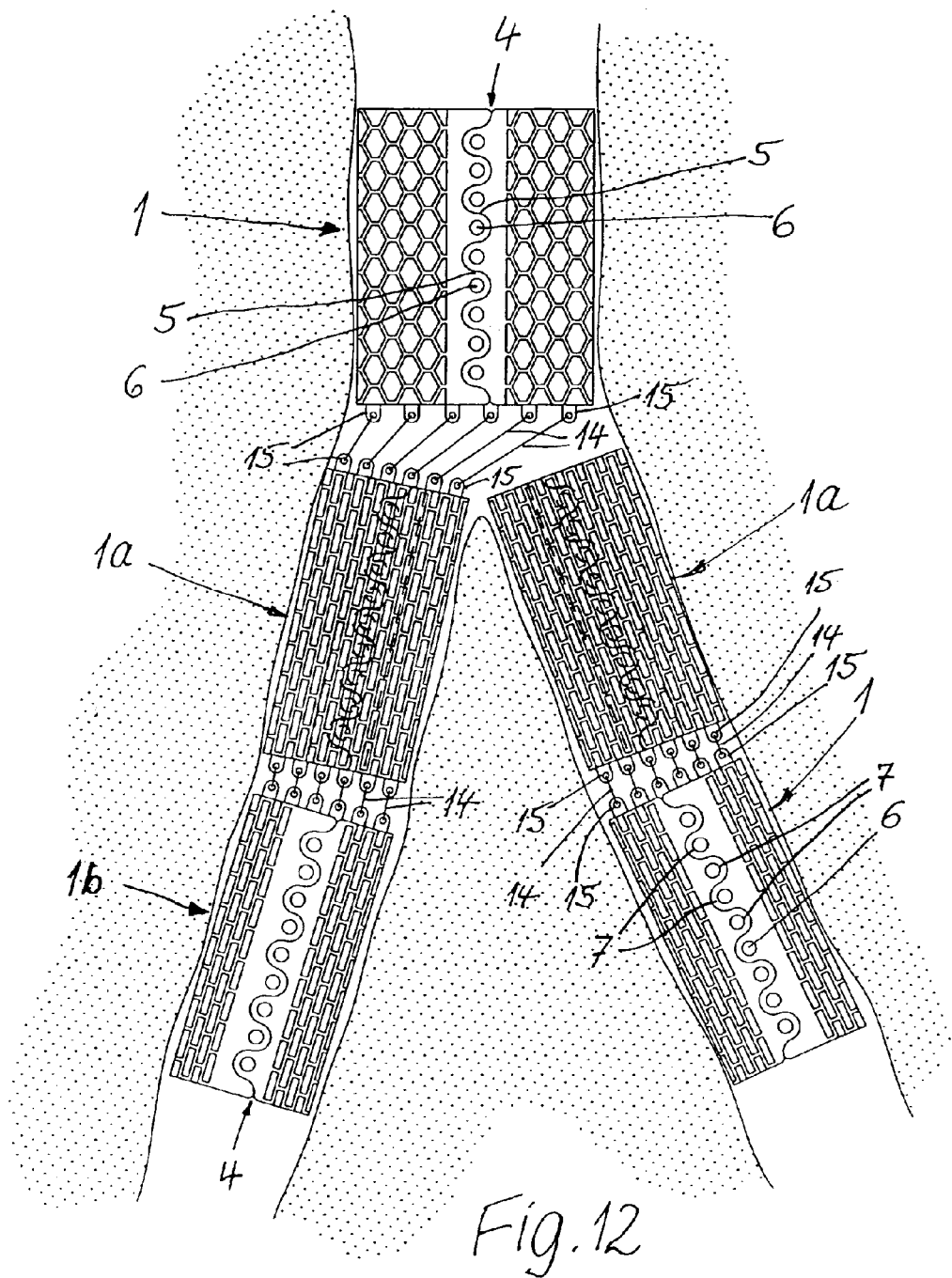
FIG. 12 is a view showing the arrangement of several continuous stents of the invention in the region of a vascular branching, whereby one of three stents is strongly dilated before the branch while the associated further connected stents are installed in an arm of the branching and dilated in accordance with the conditions there, and in the second arm of the branching two further stents continuous with each other are arranged independently of the first three stents.

In FIGS. 9 to 13, it is represented that at the end or at least one front face 10 and/or 11 of the stent 1, mobile, pliable and/or elastic connecting elements 14 are provided for fixed or separable joining with a stent 1 in a further stent 1a continuing in an approximately axial direction. Here one will recognize in these embodiments that in any given case eyelets 15 or recesses or the like of stents 1, 1a and 1b are provided on front faces 10 and/or 11 facing each other which are joined through self-dissolving threads 14 in particular which, in accordance with FIG. 2, allow laterally directed relative motions and make it to expand larger areas of a vessel in a suitable manner, if need be also with varying strength. Above all, FIGS. 10 and 11 show possibilities as to how continuous stents 1, 1a and 1b can be variously strongly expanded in order to allow for different vascular segments and dimensions. If the connection elements 14 dissolve on front faces 10 and 11, the mobility and adaptability of a corresponding vessel improves despite stents inserted over a relatively great length.

Overall there result stents 1 which on the basis of a break 4 running over the entire length no longer need be made of a metal tube and be cut meander-like axially, but can be manufactured as a flat metal piece, similar to the cutting foil of an electric razor, for example, by etching. Here the problem of a subsequent, under certain circumstances even repeated dilation, that means a subsequent further enlargement of the stent 1, for example conditioned by the growth of the patient, can be solved. The stents 1 of the invention can be used as previous stents in the human body, but can be once again expanded later if required. For increasing flexibility, several stents can be arranged axially one after the other and can be selectively expanded in such a row arrangement as needed. In this way, vascular branchings can also be well treated in accordance with FIG. 12. By selecting the material of the self-dissolving threads, the point in time of their dissolution can be selected in advance. If need be, the idea of stent connected axially one after the other can also be developed such that these individual stents are axially very short or annular, and thus a single stent with a very flexible walling is formed.

In the embodiments represented, the stent is made of a metal such as steel or high grade steel so that already the first expansion in accordance with FIG. 7 and 8 takes place with the aid of a balloon catheter 2. Instead of this, it is also possible to configure a stent 1 of memory alloy steel that is self-expanding so that a first expansion takes place according to insertion due to this memory effect of the material of the stent 1. Then later a redilation can take place in the manner described with the aid of a balloon catheter 2, whereby owing to the flexibility of such a memory metal, for example nitinol, a second, correspondingly further stent is insertable into the first stent 1 with the aid of a balloon catheter 2.

The implantable stent 1, which is installed as support sleeve in the region of a vascular constriction that is expandable, especially by means of a balloon catheter, is continuously broken along a long side. On both sides of the break 4, recesses, eyelets or punchings 6 are provided on which at least one removable holding element engages in order to keep the break 4 closed at first. After removing the holding element by extraction of or gradual dissolution of its material, the break 4 can be opened so that the previously expanded stent 1 can subsequently be further expanded by enlarging the opening 4 in order, for example, to take the growth of a patient into consideration.

What is claimed is:

1. Implantable stent which is insertable as a support sleeve in a region of a vascular constriction that is initially expandable by means of a balloon catheter, the stent comprising a wall that is expandable radially and has a continuous break along at least one longitudinal side, openings are provided on edges that extend axially on both sides of the break, in a first working position the openings are covered and penetrated by at least one removable holding element so that the break is held closed or at a specified slot spacing during the initial expansion upon insertion, the axially extending break has at least one of a wave-like, zigzag or meander-like course, and includes tongues along one of the edges that are oriented in a first peripheral direction that engage in between tongues along the other of the edges that are oriented in an opposite peripheral direction, and wherein the openings are arranged in the tongues, and the stent is further radially expandable upon removal or dissolution of the removable holding element.

2. Stent according to claim 1, wherein the openings on the two edges that are interdigitated with each other by means of tongues are generally arranged on a line running approximately axially and are acted upon by an axially and/or radially oriented holding element.

3. Stent according to claim 2, wherein the removable holding element that keeps the break of the stent together is at least one of a thread, a plastic band or a large number of rivets and is formed of a material which dissolves in the body of the patient.

4. Stent according to claim 2, wherein the removable holding element is a wire or stylet made of metal.

5. Stent according to claim 4, wherein a holding element or drawn thread engaging through the openings along the break is a surgical sewing thread which in particular runs from a front fact of the stent to an opposite face and from there back again through the openings, and wherein beginning and end of the holding element or thread are connected with each other.

6. Stent according to claim 1, wherein the stent is constructed in a flat, unrolled form, and is shaped into a support sleeve which is held together on the edges facing one another according to the shaping of the sleeve by a holding element connecting the openings, wherein the holding element comprises a wire or a thread.

7. Stent according to claim 1, wherein, on at least one front face of the stent, at least one of a removable, pliable or elastic connection element is provided for connecting with an additional stent that extends in an approximately axial direction.

8. Stent according to claim 7, wherein on adjacent faces of the stents to be joined with another of the stents and, in each case eyelets or recesses are provided which are connected by especially dissolving threads.

9. Stent according to claim 1, wherein the stent is made of metal.

10. Stent according to claim 1, wherein the stent is made of a self-expanding-shape memory alloy.

11. Stent according to claim 10, wherein the shape memory alloy is nitinol.

* * * * *